US010772607B2

(12) United States Patent
Manjo et al.

(10) Patent No.: US 10,772,607 B2
(45) Date of Patent: Sep. 15, 2020

(54) SUBJECT INFORMATION ACQUISITION APPARATUS, SUBJECT INFORMATION ACQUISITION METHOD, AND PROGRAM (71) Applicant: CANON KABUSHIKI KAISHA, Tokyo (JP)

(72) Inventors: Takahiro Manjo, Kyoto (JP); Hirofumi Taki, Kyoto (JP); Toru Sato, Kyoto (JP); Masaharu Akao, Kyoto (JP); Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 129 days.

(21) Appl. No.: 15/119,363

(22) PCT Filed: Feb. 2, 2015

(86) PCT No.: PCT/JP2015/000441
§ 371 (c)(1),
(2) Date: Aug. 16, 2016

(87) PCT Pub. No.: WO2015/125419
PCT Pub. Date: Aug. 27, 2015

(65) Prior Publication Data
US 2017/0055954 A1    Mar. 2, 2017

(30) Foreign Application Priority Data

Feb. 19, 2014 (JP) ................... 2014-029732

(51) Int. Cl.
A61B 8/08    (2006.01)
A61B 8/04    (2006.01)
(Continued)

(52) U.S. Cl.
CPC .............. *A61B 8/481* (2013.01); *A61B 5/022* (2013.01); *A61B 5/02108* (2013.01); *A61B 8/02* (2013.01);
(Continued)

(58) Field of Classification Search
CPC ....... A61B 5/02108; A61B 5/022; A61B 8/02; A61B 8/04; A61B 8/0883; A61B 8/14;
(Continued)

(56) References Cited

U.S. PATENT DOCUMENTS 4,265,251 A    5/1981 Tickner
5,749,364 A *  5/1998 Sliwa, Jr. ................. A61B 8/08
                                                        600/438

(Continued)

FOREIGN PATENT DOCUMENTS

JP    5341995 B2    11/2013

OTHER PUBLICATIONS

B. Williams, et al., "Differential Impact of Blood Pressure-Lowering Drugs on Central Aortic Pressure and Clinical Outcomes", Circulation (a journal published by the American Heart Association), Mar. 7, 2006, pp. 1213-1225, vol. 113, http://www.ncbi.nlm.nih.gov/pubmed/16476843.

*Primary Examiner* — Christopher Koharski
*Assistant Examiner* — James Moss
(74) *Attorney, Agent, or Firm* — Canon U.S.A., Inc., IP Division (57) ABSTRACT A subject information acquisition apparatus includes a converter configured to receive reflected waves from a contrast medium within a target area inside a subject, and a pressure information acquisition unit configured to acquire pressure information within the target area. In this case, the converter receives reflected waves from a contrast medium in each of a first period and a second period in which a pressure within the target area is different from the first period. The pressure information acquisition unit acquires pressure information in the second period within the target area based on a receive signal based on reflected waves in the first period, a receive signal based on a reflected wave in the second period, and (Continued)

pressure information on a region different from the target area, the pressure information being acquired in the first period.

22 Claims, 4 Drawing Sheets

(51) Int. Cl.
| | |
|---|---|
| *G01S 7/52* | (2006.01) |
| *A61B 5/022* | (2006.01) |
| *A61B 5/021* | (2006.01) |
| *G01S 15/89* | (2006.01) |
| *A61B 8/02* | (2006.01) |
| *A61B 8/14* | (2006.01) |
| *A61B 8/00* | (2006.01) |
| *G01S 7/58* | (2006.01) |

(52) U.S. Cl.
CPC .............. *A61B 8/04* (2013.01); *A61B 8/0883* (2013.01); *A61B 8/14* (2013.01); *A61B 8/461* (2013.01); *A61B 8/5207* (2013.01); *A61B 8/5223* (2013.01); *G01S 7/52039* (2013.01); *G01S 15/8915* (2013.01); *G01S 7/58* (2013.01)

(58) Field of Classification Search
CPC ....... A61B 8/461; A61B 8/481; A61B 8/5207; A61B 8/5223; G01S 7/52039; G01S 7/58; G01S 15/8915
USPC ......................................................... 600/431
See application file for complete search history.

(56) References Cited

U.S. PATENT DOCUMENTS

| | | | | |
|---|---|---|---|---|
| 6,302,845 | B2 * | 10/2001 | Shi | A61B 8/04 600/438 |
| 2003/0083582 | A1 * | 5/2003 | Hirsh | A61B 5/02028 600/509 |
| 2004/0059220 | A1 * | 3/2004 | Mourad | A61B 5/0048 600/442 |
| 2007/0078344 | A1 * | 4/2007 | Rafter | A61B 8/08 600/450 |

* cited by examiner

SUBJECT INFORMATION ACQUISITION APPARATUS, SUBJECT INFORMATION ACQUISITION METHOD, AND PROGRAM

TECHNICAL FIELD

The present invention relates to a subject information acquisition apparatus, a subject information acquisition method, and a program. The present invention particularly relates to a technology which transmits acoustic waves to a subject, receives waves reflected inside a subject and acquires pressure information on a target area within a subject.

BACKGROUND ART

Ultrasonic diagnostic apparatuses which are subject information acquisition apparatuses have been widely used in medical sites, for example. Such apparatuses are applicable widely and are aimed for many regions including the heart.

A blood pressure is importantly measured in heart disease inspections and diagnoses. Methods for measuring a blood pressure which are performed in real medical sites may include a bloodless measurement to be performed by winding a cuff around an upper arm, for example, and a bloody measurement to be performed by inserting a catheter into a blood vein.

PTL 1 discloses a method for measuring endocardial pressure by injecting an ultrasonic contrast medium (hereinafter, simply called a "contrast medium") containing fine bubbles into a blood vein and analyzing a frequency distribution of a signal component based on reflected waves from the contrast medium.

CITATION LIST

Patent Literature

PTL 1: Japanese Patent No. 5341995

SUMMARY OF INVENTION

Technical Problem

A bloodless measurement is noninvasive but does not continuously measure an endocardial pressure itself. Particularly, in a case where a heart valve is closed and traffic between a pressure measurement region subject to a bloodless measurement and inside of the heart is shut down, it may be difficult to infer endocardial pressure from the pressure in the measurement region. A bloody measurement using a catheter is highly invasive. Therefore, an endocardial pressure measurement method which is highly accurate and low invasive has been demanded.

A method using a contrast medium as disclosed in PTL 1 is low invasive and may possibly measure endocardial pressure itself. However, improved accuracy of acquisition of pressure information has been demanded.

In view of these problems, the present invention acquires pressure information on inside of a target area with high accuracy.

Solution to Problem

A subject information acquisition apparatus according to an aspect of the present invention includes a converter configured to receive reflected waves from a contrast medium within a target area inside a subject and output time-series receive signals, and a pressure information acquisition unit configured to acquire pressure information within the target area. In this case, the converter receives reflected waves from a contrast medium in each of a first period and a second period in which a pressure within the target area is different from the first period. The pressure information acquisition unit acquires pressure information in the second period within the target area based on a receive signal based on reflected waves in the first period, a receive signal based on a reflected wave in the second period, and pressure information on a region different from the target area, the pressure information being acquired in the first period.

According to a method using a contrast medium as disclosed in PTL 1, bubbles contained in a contrast medium highly interact with surrounding bubbles and have a behavior influenced by the surrounding bubbles. For example, a resonance frequency calculated by using a theoretical formula considering a structure of bubbles is higher than a resonance frequency inferred from a shape of a frequency spectrum that a signal based on reflected waves from bubbles actually has. The present invention may solve such a problem and allow acquisition of pressure information on inside of a target area with high accuracy.

Advantageous Effects of Invention

According to the present invention, pressure information on inside of a target area may be acquired with high accuracy.

Further features of the present invention will become apparent from the following description of exemplary embodiments with reference to the attached drawings.

DESCRIPTION OF EMBODIMENTS

An embodiment of the present invention will be described below with reference to drawings. Like numbers in principle refer to like parts, and the description will be omitted.

According to the present invention, an acoustic wave typically refers to an ultrasonic wave and may include an elastic wave called a sonic wave or an ultrasonic wave. A subject information acquisition apparatus according to the present invention may include an apparatus which transmits acoustic waves to a subject, receives reflected waves (reflected acoustic wave) from inside of the subject and acquires information on inside of the subject as a numerical value or image data. The information on inside of a subject to be acquired may include pressure information, information reflecting a difference in acoustic impedance between tissues, movement information and so on. The pressure information may include information regarding blood pressure and particularly describes endocardial pressure inside the heart. The information reflecting a difference in acoustic impedance may include an acoustic characteristic distribution on a tomogram such as a B-mode image or a three-dimensional image, for example. The movement information may include speed information describing a blood flow and Doppler information.

It should be noted that an embodiment of the present invention focuses on interactions between bubbles contained in a contrast medium. Regarding a behavior of a single bubble, because the diameter of a single bubble changes in accordance with a surrounding pressure, its frequency spectrum changes in accordance with the surrounding pressure. However, in reality, as the presence concentration of bubbles increases, the influence of an interaction between the bubbles increases. Thus, the resulting frequency spectrum shifts to a lower frequency side. In other words, a characteristic of reflected waves from bubbles may change in accordance with the presence concentration of the bubbles. According to an embodiment of the present invention, pressure information within a target area is acquired in consideration of information regarding a presence concentration of bubbles. The "presence concentration" herein refers to a number of bubbles per unit volume.

First Embodiment

An apparatus configuration and a processing flow according to a first embodiment will be described below.

Configuration of Subject Information Acquisition Apparatus

Figure 1:
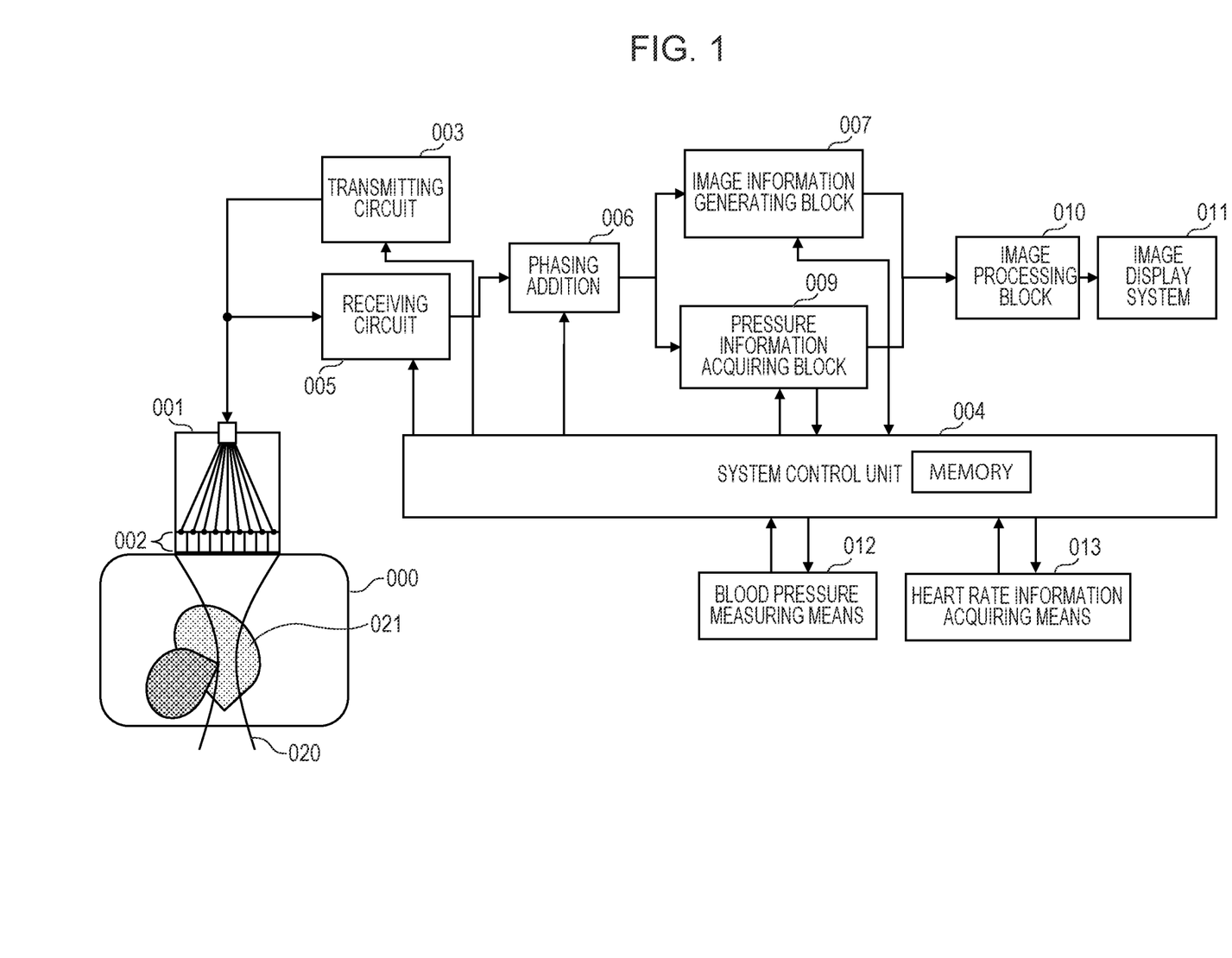
FIG. 1 is a schematic diagram illustrating an outline of a subject information acquisition apparatus according to a first embodiment.

FIG. 1 is a schematic diagram illustrating a configuration of a subject information acquisition apparatus according to the first embodiment. The subject information acquisition apparatus according to this embodiment includes a probe 001 having a plurality of converters 002, a receiving circuit 005, a transmitting circuit 003, and a phasing addition block 006. The subject information acquisition apparatus further includes an image information generating block 007, a pressure information acquiring block 009, an image processing block 010, an image display system 011, and a system control unit 004.

The probe 001 is a transceiver configured to transmit acoustic waves to a subject 000 and receive reflected waves from a plurality of positions inside the subject and includes the plurality of converters 002 configured to convert acoustic waves to an electric signal (time series received signal). A target area 021 (such as an area inside the left ventricle) is inside the subject 000. Acoustic waves are transmitted from a plurality of converters 002 such that an ultrasonic wave transmit beam (virtually referred by 020) may move inside the target area 021. Reflected waves from the target area 021 are received from the plurality of converters 002. Each of the converters 002 may receive acoustic waves and convert them to an electric signal and may be a piezoelectric element using a piezoelectric phenomenon and a converter using resonance of light or a converter using a change in capacitance as in CMUT. The plurality of converters may be arranged in 1D array, 1.5D array, 1.75D array, 2D array or the like.

The transmitting circuit 003 is a transmit signal generator configured to generate a transmit signal (pulse signal) having a voltage waveform having a delay time period or amplitude based on the position of interest or direction of interest according to a control signal from the system control unit 004. Such a transmit signal is converted to acoustic waves input to the plurality of converters 002, and the acoustic waves are transmitted as acoustic wave pulses (pulse waves). The transmitting circuit 003 may include a multiplexer and a switch. Reflected waves from a subject are received by the plurality of converters 002, and a plurality of receive signals output from the plurality of converters 002 are input to the receiving circuit 005.

The receiving circuit 005 is a receive signal processor configured to amplify the receive signals output in a time-series manner from the converters and convert them to digital signals (digitalized receive signals) and may include an amplifier and an A/D converter. It should be noted that the number of channels of the receiving circuit 005 may not always equal to the number of converters 002. Typically, the number of the converters 002 may be lower than the number of channels of the receiving circuit 005. For example, in a case where 32 converter units of 256 converters perform beam forming, the receiving circuit may have 32 channels. Receive signals output from the channels of the receiving circuit 005 are input to the phasing addition block 006.

The phasing addition block 006 is a receive beam former operative according to a control signal from the system control unit 004. More specifically, a what-is-called phasing addition process is performed which is a process for adjusting phases of input signals and then adding them based on information (delay time period information) describing a time taken by reflected waves to arrive from a predetermined position to the converters 002. The phase adjustment may include a process for reading a signal component of an address corresponding to the delay time period from a memory storing receive signals in a time-series manner after digitally converted channel by channel. The phasing addition block 006 may include a storage medium such as an FIFO memory and a random access memory and an adder. The receive data having undergone the phasing addition are input to the image information generating block 007 and the pressure information acquiring block 009.

The image information generating block 007 is a distribution generation unit configured to generate a distribution (distribution data such as B-mode image, M-mode image, and Doppler image) of characteristic information corresponding to a position inside a subject by using input receive data. More specifically, a band pass-filter is applied to the input receive data and their envelop is calculated (envelop detection) to generate two-dimensional or three-dimensional distribution data. The generated distribution data are input to the image processing block 010.

Figure 2:
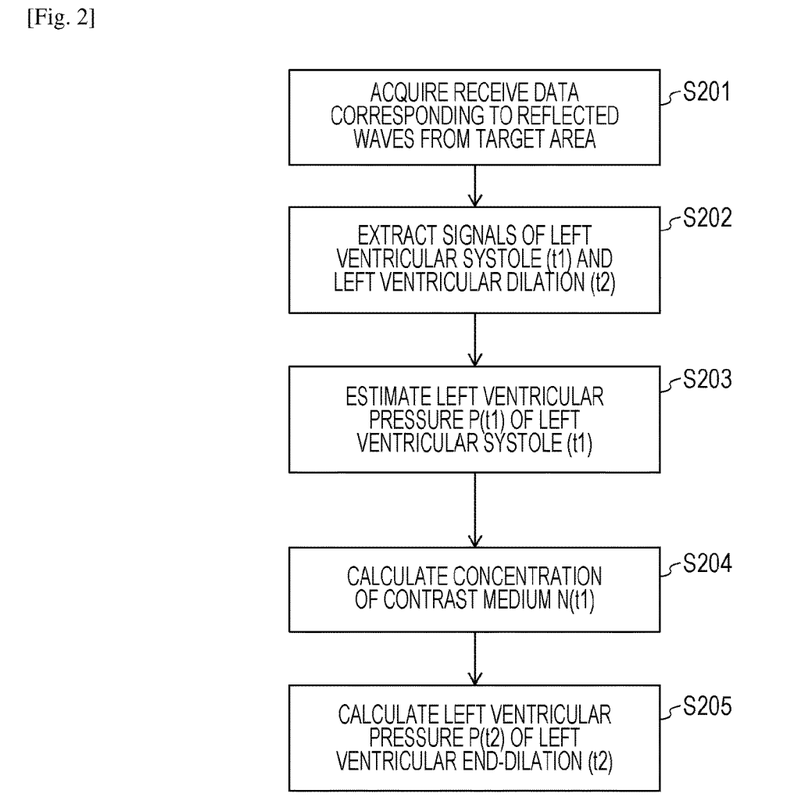
FIG. 2 is a flowchart illustrating a processing flow of the first embodiment.

The pressure information acquiring block 009 is a pressure information acquisition unit configured to acquire pressure information on inside of a target area 021 based on the receive data input from the phasing addition block 006 and data input from the system control unit 004 by using a method, which will be described with reference to FIG. 2. The acquired pressure information is input to the image processing block 010.

The image processing block 010 applies edge highlighting and an image filter on distribution data input from the image information generating block 007. The image processing block 010 uses pressure information input from the pressure information acquiring block 009 to generate and output display data to be displayed finally. More specifically, the image processing block 010 may display a B-mode image and the pressure information on one screen, as in a second embodiment.

The system control unit 004 is a control unit configured to transmit a control signal to a component and receive information from a component. The system control unit 004 includes a memory holding a table regarding three parameters, which will be described below.

The image display system 011 is a display unit configured to display an image based on display data output from the image processing block 010. The image display system 011 may be an LCD (Liquid Crystal Display), a CRT (Cathode Ray Tube), or an organic EL display, for example. It should be noted that the image display system 011 may not be provided in a subject information processing apparatus of the present invention and may be separately provided and be connected to the subject information acquisition apparatus.

Each of the image information generating block 007, pressure information acquiring block 009, image processing block 010, and system control unit 004 may include a memory and a processor such as a CPU, an MPU and a GPU (Graphics Processing Unit) or may include an FPGA (Field Programmable Gate Array) chip. Such a memory may include a storage medium such as a ROM, a RAM, and a hard disk. The storage unit may include a plurality of storage media instead of one storage medium.

A contrast medium to be used may contain a plurality of bubbles each having a diameter smaller than 100 micrometers such as micro bubbles or nano bubbles. More specifically, as disclosed in PTL 1, such a contract medium may contain bubbles without shells, bubbles internally containing shells of biodegradable polymers or bubbles having shells internally containing liquid.

Processing Flow of Pressure Information Acquisition Block

Figure 3A:
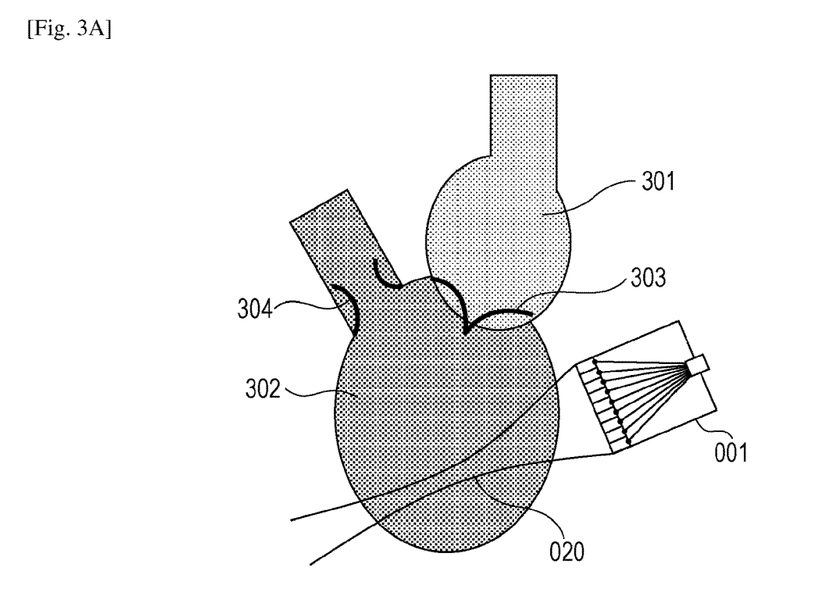
FIG. 3A is a conceptual diagram illustrating an operation of the heart.
Figure 3B:
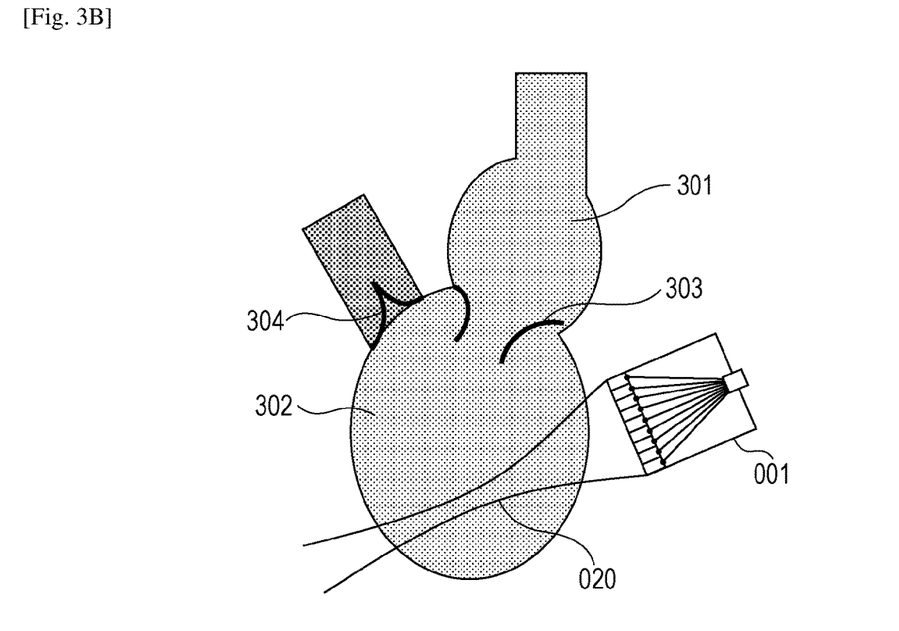
FIG. 3B is a conceptual diagram illustrating an operation of the heart.

Next, with reference to FIG. 2 and FIGS. 3A and 3B, operations of the pressure information acquiring block 009 will be described. FIG. 2 is a flowchart illustrating a processing flow of this embodiment. FIGS. 3A and 3B are conceptual diagrams illustrating operations of the heart for explaining an example of this embodiment.

In a case where myocardial infarction is developed, endocardial pressure of a left ventricular end-dilation may be measured in order to predict a degree of seriousness and a poor prognosis such as pulmonary edema. A method for measuring a left ventricular end-diastolic pressure, for example, will be described below. As described above, the present invention focuses on a presence concentration of bubbles for measuring a pressure. According to this embodiment, a state of a left ventricular systole is used for acquiring a presence concentration of bubbles within the left ventricle in a left ventricular end-dilation. A left ventricular systole has a different endocardial pressure from that of a left ventricular end-dilation.

FIG. 3A illustrates a left ventricular systole in which a left ventricle 302 contracts and an aortic valve 304 opens. FIG. 3B illustrates a left ventricular end-dilation in which blood flows from a left atrium 301 to the left ventricle 302 and a mitral valve 303 opens.

According to this embodiment, the probe 001 transmits ultrasonic wave pulses a plurality of number of times to a target area inside the left ventricle 302 when a contrast medium exists in the left ventricle 302 and receives the reflected waves from the area. The pressure information acquiring block 009 acquires receive data based on the reflected waves in step S201. Ultrasonic waves are transmitted at least once and are received at least once in each of periods of a left ventricular systole and a left ventricular end-dilation.

Next, in step S202, the pressure information acquiring block 009 extracts signals corresponding to a left ventricular systole (first period t1) and a left ventricular end-dilation (second period t2) from the receive data. These signals will be called S(t1) and S(t2), respectively. The timings of a left ventricular systole and a left ventricular end-dilation may be acquired based on an output result from a heartbeat information acquisition unit 013 configured to acquire information regarding the heartbeat (heartbeat), such as an electrocardiograph for acquiring an electrocardiogram, a heartbeat monitor, and a phonocardiograph. According to this method, because a left ventricle, for example, is extracted by using an ultrasonic echo, the heartbeat information may be acquired from an ultrasonic echo image. More specifically, the system control unit 004 first detects heartbeats from distribution data generated by the image information generating block 007. Based on the information from the image information generating block 007, the system control unit 004 transmits timings of a left ventricular systole and a left ventricular end-dilation to the pressure information acquiring block 009. In other words, based on a B-mode image, an M-mode image, a Doppler image or the like, timings of a left ventricular systole and a left ventricular end-dilation may be acquired.

According to this embodiment, because the heartbeat information acquisition unit 013 is connected to the system control unit 004, the system control unit 004 transmits timings of a left ventricular systole and a left ventricular end-dilation to the pressure information acquiring block 009 based on the input heart-beat-related information. It should be noted that the heartbeat information acquisition unit 013 may not be included in a subject information processing apparatus of the present invention but may be provided separately and be connected to the subject information acquisition apparatus.

Next, in step S203, the pressure information acquiring block 009 acquires an endocardial pressure P(t1) inside the left ventricle in a left ventricular systole (t1). Here, in a left ventricular systole, an aortic valve 304 between the left ventricle 302 and an aortic root opens as illustrated in FIG. 3A. Therefore, in this period, a blood pressure inside the left ventricle 302 and a blood pressure of the aortic root may be approximated. A blood pressure of an aortic root may be acquired by performing upper arm blood pressure measurement using a cuff, which is a bloodless measurement, as disclosed in "Williams B et al. Circulation, 113, 1213-1225, 2006".

According to this embodiment, a blood pressure measurement unit 012 (pressure measurement device) for measuring a blood pressure of an upper arm is connected to the system control unit 004, and the system control unit 004 inputs the input blood pressure information to the pressure information acquiring block 009. The pressure information acquiring block 009 acquires an endocardial pressure P(t1) inside a left ventricle in the left ventricular systole t1 based on the input blood pressure information.

A blood pressure monitor which is the blood pressure measurement unit 012 may not be included in a subject information processing apparatus of the present invention but may be provided separately and be connected to the subject information acquisition apparatus.

Next, in step S204, the pressure information acquiring block 009 acquires a presence concentration N(t1) of a contrast medium by using a signal S(t1) in the left ventricular systole (t1) and the endocardial pressure P(t1). The endocardial pressure P(t1) in the left ventricular systole acquired in S203 may be stored once in the system control unit 004 and may be input again to the pressure information acquiring block 009 in step S204.

The pressure information acquiring block 009 acquires a frequency spectrum of a contrast medium echo from the signal S(t1). Regarding the frequency spectrum, a spectrum of the signal S(t1) is calculated, and a frequency spectrum of a contrast medium echo contained in the spectrum may be inferred by using a proper filter. The "proper filter" may refer to one configured to allow a signal having a frequency near a frequency based on a transmission frequency to pass through and allows extraction of a frequency near a main component contained in a waveform occurring from bubbles. The filter may allow a frequency near a high-frequency of a waveform occurring from bubbles to pass through. A characteristic may further be extracted from the inferred frequency spectrum by using a frequency having a peak intensity, a value of a first moment of the spectrum, a total amount of energy, a ratio calculated from a plurality of frequency spectra.

Here, the system control unit 004 has a memory storing a table describing a relationship among three parameters of information regarding a presence concentration N(t) of a contrast medium, a frequency spectrum (information regarding a frequency) of a contrast medium echo, and pressure information on surroundings of the contrast medium. The relationship among the three parameters may be measured in advance and may be stored in the memory.

The system control unit 004 transmits the table information to the pressure information acquiring block 009. With reference to the relationship among the three parameters (a presence concentration, a frequency spectrum, and a surrounding pressure), the pressure information acquiring block 009 may acquire one parameter (presence concentration) because two parameters of them (frequency spectrum and surrounding pressure) are already given.

Finally in step S205, the pressure information acquiring block 009 uses a receive signal S(t2) in a left ventricular end-dilation (t2) and a presence concentration N(t2) of the contrast medium in a left ventricular end-dilation to acquire an endocardial pressure P(t2).

More specifically, the pressure information acquiring block 009 acquires a frequency spectrum of a contrast medium echo from the signal S(t1). Regarding the frequency spectrum, a spectrum of a signal S(t2) may be calculated, and a frequency spectrum of a contrast medium echo contained in the spectrum may be acquired. The presence concentration N(t2) of the contrast medium may be N(t1) acquired in step S204. Therefore, an approximation of N(t2)=N(t1) is acquired. This is because the left ventricular systole t1 and the left ventricular end-dilation t2 occur in significantly close timings and because the presence concentration of the contrast medium inside the left ventricle may hardly change. Particularly, in an interval from the left ventricular end-dilation t2 to the left ventricular systole t1, a valve is closed between the left atrium and the left ventricle so that new blood does not enter into the left ventricle. Thus, it may be regarded that the concentration (the number of bubbles per unit volume) does not change in the interval. Accordingly, the measurement is performed first in the left ventricular end-dilation t2, and the measurement may be performed in the left ventricular systole t1 subsequently. In other words, in a time series, after ultrasonic waves for acquiring the S(t2) are transmitted and received, ultrasonic waves for acquiring the S(t1) may be transmitted and received.

Therefore, the pressure information acquiring block 009 determines the two parameters (frequency spectrum and presence concentration). Based on the relationship among the three parameters (presence concentration, frequency spectrum, and surrounding pressure), the remaining parameter, the surrounding pressure, that is, the endocardial pressure P(t2) may be finally acquired.

According to this embodiment, as described above, an endocardial pressure in a left ventricular end-dilation may be measured based on a receive signal based on reflected waves acquired in a left ventricular systole and a left ventricular end-dilation and an upper arm blood pressure (pressure in a different region from a target area) acquired in the left ventricular systole.

Effects of This Embodiment

Next, effects of this embodiment will be described. First, a relationship among the three parameters of a contrast medium will be described. As described above, regarding a behavior of a single bubble contained in a contrast medium, because a diameter of a single fine bubble is changed by a surrounding pressure, a frequency spectrum may change in accordance with the surrounding pressure. However, in reality, as the presence concentration of bubbles increases, an influence of an interaction between bubbles increases and a resulting frequency spectrum decreases. In other words, a characteristic of reflected waves from bubbles may change in accordance with the presence concentration of the bubbles.

The presence concentration of a contrast medium, the frequency characteristic of reflected waves, and a surrounding pressure of the contrast medium are parameters which are correlated with each other. Therefore, even when one parameter (such as a frequency characteristic) may be measured, it is difficult to accurately calculate a surrounding pressure of the contrast medium.

This embodiment focuses on the relationship among the three parameters, and a presence concentration of a contrast medium in a left ventricular systole is calculated based on an endocardial pressure inferred from a pressure measured in a different region and a frequency characteristic acquired from a signal corresponding to reflected waves. Furthermore, the embodiment further uses the fact that the presence concentration of a contrast medium inside the left ventricle does not change in a left ventricular end-dilation and a left ventricular systole which are continuous.

In other words, a surrounding pressure of a contrast medium in a left ventricular end-dilation may be calculated by using an identical value to that of the presence concentration in a left ventricular systole to the value of a presence concentration of a contrast medium in a left ventricular end-dilation and acquiring a frequency spectrum by using a signal corresponding to reflected waves inside the left ventricle in the left ventricular end-dilation.

Thus, such a pressure may be calculated with high accuracy in consideration of a parameter of a presence concentration of a contrast medium.

According to this embodiment, a frequency spectrum is used as one of three parameters, for example. However, the effects of the present invention may be acquired by focusing on a characteristic of reflected waves from a contrast medium which changes in accordance with a surrounding pressure of the contrast medium. For example, in a case where the size of a high-frequency component or a low-frequency component resulting from a nonlinear behavior of bubbles is used, a filter may be used which allows a specific frequency component to pass through.

A characteristic of a waveform reflected from bubbles changes in accordance with a frequency of transmitted ultrasonic pulses or a width of the pulse. A plurality of tables describing a relationship among three parameters may be prepared correspondingly to a frequency of transmitted ultrasonic pulses or a width of the pulse, and one of the tables corresponding to a given pulse may be used. Use of such a plurality of tables may allow highly reliable calculation of an endocardial pressure.

A characteristic of a waveform reflected from bubbles may change also in accordance with a depth inside a subject. Accordingly, a plurality of tables describing a relationship among three parameters may be prepared in accordance with a depth of a target area, and one of the tables corresponding to the depth may be used. Use of such a plurality of table may allow highly reliable calculation of an endocardial pressure.

According to this embodiment, ultrasonic wave pulses are transmitted and received a plurality of number of times continuously, and the pressure information acquiring block 009 in a subsequent stage extracts signals in a left ventricular end-dilation and a left ventricular systole. However, the timings of transmission and reception of ultrasonic waves may be controlled. In other words, the timings of a left ventricular end-dilation and a left ventricular systole may be acquired based on an output from the heartbeat information acquisition unit 013, and ultrasonic waves may be transmitted and reflected waves may be received only in the timings of a left ventricular end-dilation and a left ventricular systole.

According to this embodiment, an endocardial pressure in a left ventricular end-dilation handled as the second period. However, an endocardial pressure may be acquired in other timings as far as the timings are in a dilation, instead of an end-dilation.

Second Embodiment

Next, a second embodiment will be described. According to this embodiment, displays of timings of processing and pressure information in the pressure information acquiring block 009 will be described. A subject information acquisition apparatus of this embodiment has the same components as those of the first embodiment. Like numbers refer to like component in the first and second embodiments, and the description will be omitted.

Figure 4:
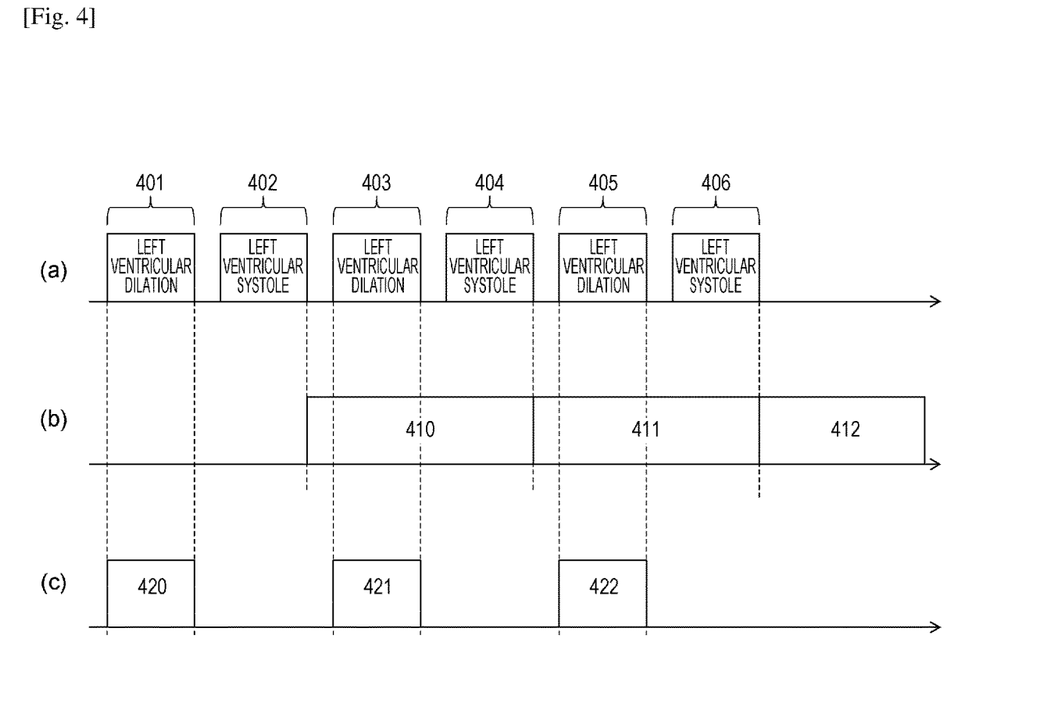
FIG. 4 is a schematic diagram illustrating a relationship between operations of the left ventricle of the heart and displays of endocardial pressure.

FIG. 4 is a schematic diagram illustrating a relationship between operations of the left ventricle of the heart and displays of endocardial pressures. FIG. 4 schematically illustrates timings of operations of the left ventricle of the heart in (a). FIG. 4 schematically illustrates endocardial pressure display periods in (b) and (c). Like the first embodiment, an operation of the left ventricle may be acquired based on outputs from the heartbeat information acquisition unit 013 or the image information generating block 007.

New blood does not enter into the left ventricle between the end of a left ventricular dilation 401 and a left ventricular systole 402. Accordingly, a supposition that presence concentrations of a contrast medium agree between the end of the left ventricular dilation 401 and the left ventricular systole 402 is satisfied with high accuracy. Therefore, an endocardial pressure in the end of the left ventricular dilation 401 may be calculated with high accuracy by using a signal based on reflected waves acquired in the end of the left ventricular dilation 401 and in the left ventricular systole 402 and an endocardial pressure in the left ventricular systole 402 acquired based on an output from a blood pressure measurement unit. With respect to a left ventricular systole, the presence concentration of a contrast medium at beginning of the systole may be acquired. In other words, a receive signal of reflected waves at beginning of the systole and an endocardial pressure at the beginning of the systole may be used.

Though the calculated endocardial pressure is an endocardial pressure in a period at the end of the left ventricular dilation 401, the calculation ends during the left ventricular systole 402 or after the left ventricular systole ends. While a user such as a doctor is actually using the apparatus in real time (to inspect a subject), an endocardial pressure in synchronization with a B-mode image, for example, displayed in real time may not be displayed. In other words, an image of a target area of the left ventricular dilation 401 and an endocardial pressure of the left ventricular dilation 401 may not be displayed simultaneously.

In this case, an endocardial pressure in the left ventricular dilation 401 calculated at an end of the left ventricular dilation 401 and the left ventricular systole 402 may be displayed from the next end of the left ventricular dilation 403 to the time when the left ventricular systole 404 ends (until an endocardial pressure at the end of the left ventricular dilation 403 may be calculated). In other words, referring to (b) in FIG. 4, an endocardial pressure at the end of the left ventricular dilation 401 is displayed during a period 410. Such an endocardial pressure may be displayed on a bar graph or a line graph or may be represented by a numerical value. Similarly, an endocardial pressure at an end of the left ventricular dilation 403 is displayed during a period 411, and an endocardial pressure at an end of the left ventricular dilation 405 is displayed during a period 412.

By updating the display in such timings, a highly accurate endocardial pressure calculated from data without changes of a presence concentration of a contrast medium inside the left ventricle may be displayed substantially in real time, though it is one heartbeat late. Alternatively, a value may be used which is acquired by averaging left ventricular end-dilation blood pressures in a predetermined time period by using a proper forgetting coefficient.

Figure 5A:
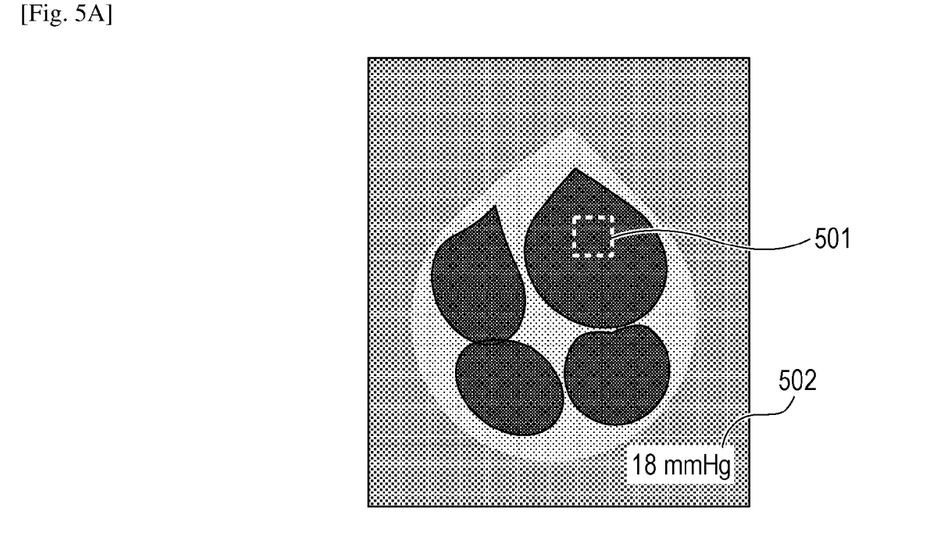
FIG. 5A is a schematic diagram illustrating an example of a display screen.
Figure 5B:
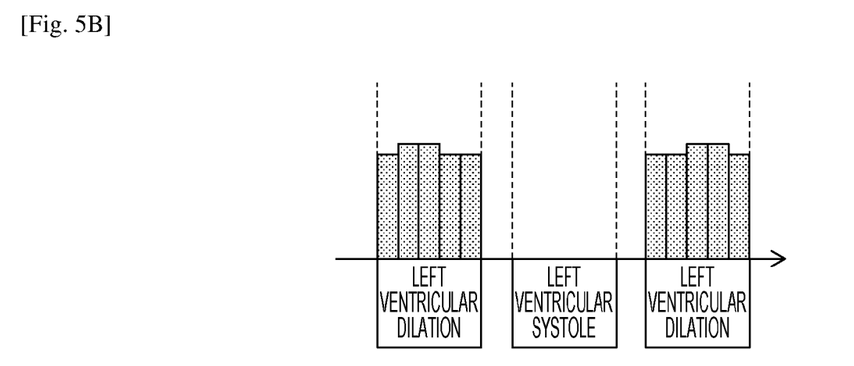
FIG. 5B is a schematic diagram illustrating an example of a display screen.
Figure 5C:
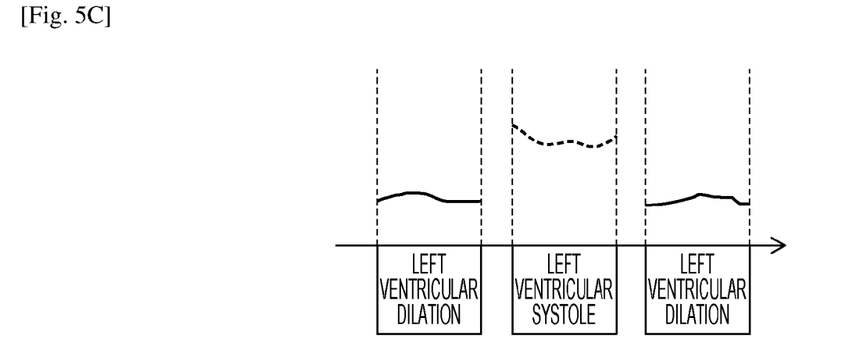
FIG. 5C is a schematic diagram illustrating an example of a display screen.

Examples of display screens according to this embodiment will be described with reference to FIGS. 5A to 5C. FIGS. 5A to 5C are schematic diagrams illustrating examples of display screens. FIG. 5A illustrates a state that a marker 501 is displayed as a guide for indicating a target area from which a pressure is to be measured on a B-mode image. An endocardial pressure calculated by using reflected waves from the target area indicated with the marker 501 is indicated by a numerical value as indicated by the reference numeral 502.

FIGS. 5B and 5C illustrate other examples of display screens of this embodiment. FIG. 5B displays endocardial pressures calculated in left ventricular dilations by using a bar graph. FIG. 5C displays endocardial pressures calculated in left ventricular dilations by using a solid line graph, and endocardial pressures calculated based on outputs from a blood pressure measurement unit in a left ventricular systole by using a broken line.

In a case where an endocardial pressure in a left ventricular dilation is calculated not during a user is inspecting a subject but by using an already acquired reflected waveform, an endocardial pressure in the left ventricular dilation 401 may be displayed in the period 420 in (c) in FIG. 4, that is, in the left ventricular dilation 401. Such timing allows display of an endocardial pressure in a left ventricular dilation in a same timing as display of a B-mode image in the left ventricular dilation.

Alternatively, while a user is using the apparatus in real time (to inspect a subject), an endocardial pressure in the left ventricular dilation 403 calculated from the left ventricular systole 402 and the left ventricular dilation 403 may be displayed in a period 421. In this case, it may be assumed that the presence concentration of a contrast medium inside the left ventricle may hardly change because the timings of the left ventricular systole 402 and the left ventricular dilation 403 are significantly close though blood is changed. Therefore, this embodiment is applicable, and an endocardial pressure may thus be calculated. Such a display timing allows display of an endocardial pressure of the left ventricular dilation 403 in the period 421, which may improve the real-time characteristic.

According to this embodiment, an endocardial pressure of one left ventricular end-dilation is calculated based on one left ventricular end-dilation and one left ventricular systole. However, endocardial pressures of a left ventricular end-dilation calculated for each heartbeat may be averaged. Thus, an influence of unintended external noise may be inhibited, and an endocardial pressure may be calculated in a stable manner and with high accuracy.

Alternatively, a frequency characteristic may be calculated based on reflected waves from a contrast medium in the left ventricular dilation 401, left ventricular dilation 403, and left ventricular dilation 405, and a frequency characteristic may be calculated based on reflected waves from the contrast medium in the left ventricular systole 402, left ventricular systole 404, and left ventricular systole 406. Then, the frequency characteristics and a blood pressure in a different region acquired by the blood pressure measurement unit 012 may be used to calculate an endocardial pressure of the left ventricle in the left ventricular dilation. Because the accuracy of calculation of a frequency characteristic by processing as described above, an endocardial pressure may be calculated with high accuracy.

Other Embodiments

The present invention may be implemented by executing the following processes. That is, the present invention may be implemented by supplying a program for implementing one or more functions of the aforementioned embodiments to a system or an apparatus over a network or a storage medium and reading and executing the program by one or more processors in a computer in the system or apparatus. It may be implemented by a circuit (such as an ASIC) which implements one or more functions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-029732, filed Feb. 19, 2014, which is hereby incorporated by reference herein in its entirety.

REFERENCE SIGNS LIST

000 Subject
001 Probe
002 Converter
003 Transmitting circuit
004 System control unit
005 Receiving circuit
006 Phasing addition block
007 Image information generating block
009 Pressure information acquisition block
010 Image processing block
011 Image display system
020 Ultrasonic wave transmit beam
021 Target area

The invention claimed is:

1. A subject information acquisition apparatus comprising:
a converter configured to receive acoustic waves from a subject into which contrast medium has been introduced, and to output receiving signals including at least a first receiving signal and a second receiving signal, the first receiving signal based on an acoustic wave during a left ventricular systole and the second receiving signal based on an acoustic wave during the left ventricular end-dilation;
a pressure information acquisition unit configured to acquire pressure information on endocardial pressure inside a left ventricle of the subject;
a memory configured to hold a table describing a relationship among information regarding a frequency of an acoustic wave acquired from a subject into which the contrast medium has been introduced, information regarding a presence concentration of the contrast medium, and pressure information on surroundings of the contrast medium,
wherein the pressure information acquisition unit acquires information regarding the presence concentration of the contrast medium within the left ventricle, by using the table, based on the first receiving signal and pressure information obtained, by a blood pressure measurement unit, from an upper arm of the subject during the left ventricular systole, and
wherein the pressure information acquisition unit determines the pressure information on the endocardial pressure inside the left ventricle of the subject, by using the relationship, during the left ventricular end-dilation based on the acquired information regarding the presence concentration of the contrast medium within the left ventricle and the second receiving signal based on the acoustic wave during the left ventricular end-dilation.

2. The subject information acquisition apparatus according to claim 1, wherein information on blood pressure of the upper arm measured by a pressure measurement device is input, as the pressure information obtained from the upper arm of the subject, to the pressure information acquisition unit.

3. The subject information acquisition apparatus according to claim 1, wherein timings of the left ventricular systole and the left ventricular end-dilation are input to the pressure information acquisition unit based on information regarding heartbeats of the subject acquired by a heartbeat information acquisition unit.

4. The subject information acquisition apparatus according to claim 3, the apparatus further comprising an image processing unit configured to update display of the pressure information on the endocardial pressure inside the left ventricle of the subject in synchronism with a heartbeat acquired from the heartbeat information acquisition unit.

5. The subject information acquisition apparatus according to claim 1, wherein the pressure information acquisition unit determines the pressure information on the endocardial pressure inside the left ventricle of the subject during the left ventricular end-dilation for each heartbeat of a plurality of heartbeats acquired by a heartbeat information acquisition unit and averages a plurality of the pressure information.

6. The subject information acquisition apparatus according to claim 1, the apparatus further comprising an image processing unit configured to display the pressure information on the endocardial pressure inside the left ventricle of the subject on a display unit.

7. The subject information acquisition apparatus according to claim 6, the apparatus further comprising a distribution generation unit configured to generate an acoustic characteristic distribution of the left ventricle by using the receiving signals output from the converter,
wherein the image processing unit displays the acoustic characteristic distribution and the pressure information on one screen of the display unit.

8. The subject information acquisition apparatus according to claim 7, wherein the image processing unit updates display of the acoustic characteristic distribution and the pressure information in synchronization with each other.

9. The subject information acquisition apparatus according to claim 1, wherein the contrast medium contains bubbles each having a shell internally containing gas.

10. The subject information acquisition apparatus according to claim 1, wherein the converter is further configured to transmit an acoustic wave to the subject.

11. A subject information acquisition method for acquiring pressure information on inside of a left ventricle of a subject, the method comprising:
transmitting acoustic waves to the subject into which contrast medium has been introduced;
receiving acoustic waves from the subject into which the contrast medium has been introduced, and outputting receiving signals including at least a first receiving signal and a second receiving signal, the first receiving signal based on an acoustic wave during a left ventricular systole and the second receiving signal based on an acoustic wave during the left ventricular end-dilation;
acquiring the receiving signals based on the acoustic waves from a left ventricle of the subject into which the contrast medium has been introduced, during each of the left ventricular systole and the left ventricular end-dilation, the left ventricular end-dilation having a different pressure inside the left ventricle from that of the left ventricular systole;
acquiring pressure information obtained from an upper arm of the subject during the left ventricular systole;
acquiring information regarding a presence concentration of the contrast medium within the left ventricle based on the first receiving signal and pressure information obtained, by a blood pressure measurement unit, from the upper arm during the left ventricular systole; and
determining pressure information on the endocardial pressure inside the left ventricle of the subject during the left ventricular end-dilation based on the second receiving signal and the information regarding the presence concentration of the contrast medium within the left ventricle.

12. A non-transitory computer-readable medium storing thereon a program for causing a computer to execute operations in the subject information acquisition method according to claim 11.

13. The method according to claim 11,
wherein the information regarding the presence concentration of the contrast medium within the left ventricle is acquired according to a relationship among information regarding a frequency of an acoustic wave acquired from a subject into which contrast medium has been introduced, information regarding a presence concentration of the contrast medium within the left ventricle, and pressure information on surroundings of the contrast medium.

14. The method according to claim 11, further comprising:
displaying, in a display unit, one or more of (a) the pressure information on the endocardial pressure inside the left ventricle, (b) information regarding the presence concentration of the contrast medium within the left ventricle, and (c) a B-mode image of the left ventricle.

15. A subject information acquisition apparatus comprising:
a converter configured to receive acoustic waves from a subject into which contrast medium has been introduced, and to output receiving signals including at least a first receiving signal and a second receiving signal, the first receiving signal based on an acoustic wave during a left ventricular systole and the second receiving signal based on an acoustic wave during the left ventricular dilation; and
a pressure information acquisition unit configured to acquire pressure information on endocardial pressure inside a left ventricle of the subject,
wherein the pressure information acquisition unit acquires information regarding a presence concentration of the contrast medium within the left ventricle based on the first receiving signal and pressure information on a blood pressure of an aortic root during the left ventricular systole, and
wherein the pressure information acquisition unit determines pressure information on the endocardial pressure inside the left ventricle during the left ventricular dilation based on the second receiving signal and the information regarding the presence concentration of the contrast medium within the left ventricle.

16. The subject information acquisition apparatus according to claim 15, wherein information on blood pressure of an upper arm measured by a pressure measurement device is input, as the pressure information on the blood pressure of the aortic root the upper arm, to the pressure information acquisition unit.

17. The subject information acquisition apparatus according to claim 15, wherein timings of the left ventricular systole and the left ventricular dilation are input to the pressure information acquisition unit based on information regarding heartbeats of the subject acquired by a heartbeat information acquisition unit.

18. The subject information acquisition apparatus according to claim 17, the apparatus further comprising an image processing unit configured to update display of the pressure information on the endocardial pressure inside the left ventricle of the subject in synchronism with a heartbeat acquired from the heartbeat information acquisition unit.

19. The subject information acquisition apparatus according to claim 15, wherein the pressure information acquisition unit determines the pressure information during the left ventricular dilation for each heartbeat of a plurality of heartbeats acquired by a heartbeat information acquisition unit and averages a plurality of the pressure information.

20. The subject information acquisition apparatus according to claim 15, the apparatus further comprising an image processing unit configured to display the pressure information on the endocardial pressure inside the left ventricle of the subject on a display unit.

21. The subject information acquisition apparatus according to claim 20, the apparatus further comprising a distribution generation unit configured to generate an acoustic characteristic distribution of the left ventricle by using the receiving signals output from the converter,
   wherein the image processing unit displays the acoustic characteristic distribution and the pressure information on one screen of the display unit.

22. The subject information acquisition apparatus according to claim 15, wherein the pressure information acquisition unit acquires information regarding the presence concentration of the contrast medium within the left ventricle according to a relationship among information regarding a frequency of an acoustic wave acquired from a subject into which contrast medium has been introduced, information regarding a presence concentration of contrast medium, and pressure information on surroundings of the contrast medium, and wherein the pressure information acquisition unit determines the pressure information on the endocardial pressure inside the left ventricle of the subject according to the relationship.

* * * * *